United States Patent [19]
Hewawasam et al.

[11] Patent Number: 5,977,150
[45] Date of Patent: Nov. 2, 1999

[54] AMINO ACID DERIVATIVES OF DIARYL 1,3, 4-OXADIAZOLONE

[75] Inventors: Piyasena Hewawasam, Middletown; Xi Chen, Killingworth; John E. Starrett, Jr., Middletown, all of Conn.

[73] Assignee: Bristol-Myers Squibb Company, Princeton, N.J.

[21] Appl. No.: 09/237,429

[22] Filed: Jan. 26, 1999

Related U.S. Application Data

[60] Provisional application No. 60/072,925, Jan. 12, 1998.
[51] Int. Cl.$^6$ ...................... C07D 271/113; A61K 31/41
[52] U.S. Cl. ............................................. 514/364; 548/144
[58] Field of Search ............................... 514/364; 548/144

[56] References Cited

U.S. PATENT DOCUMENTS

| | | |
|---|---|---|
| 3,971,803 | 7/1976 | Rosenberger et al. . |
| 5,869,509 | 2/1999 | Romine et al. . |

FOREIGN PATENT DOCUMENTS

| | | |
|---|---|---|
| 533 276 | 3/1993 | European Pat. Off. . |
| WO 98/04135 | 2/1998 | WIPO . |

OTHER PUBLICATIONS

Ahmed, F. et al., "Some Features of the Spasmogenic Actions of Acetylcholine and Histamine in Guinea–Pig Isolated Trachealis", *Br. J. Pharmacol.*, 83, pp. 227–233 (1984).

Baró, I. and Escande, D., "A $Ca^{2+}$–activated $K^+$ Current in Guinea–pig Atrial Myocytes", *Pflügers Archiv.*, 414 (Suppl. 1), pp. S168–S–170 (1989).

Cook, N.S., "The Pharmacology of Potassium Channels and Their Therapeutic Potential", *Trends in Pharmacol. Sciences*, 9, pp. 21–28 (Jan., 1988).

Koh, D–S., et al., "Effect of the Flavoid Phloretin on $Ca^{2+}$–activated $K^+$ Channels in Myelinated Nerve Fibres of *Xenopus Laevis*", *Neuroscience Lett.* 165, pp. 167–170 (1994).

Quast, U. and Cook, N. S., "Moving Together: $K^+$ Channel Openers and ATP–sensitive $K^+$ Channels", *Trends in Pharmacol. Sciences*, 10, pp. 431–435 [Nov., 1989).

Singer, J.J. and Walsh, J.V., "Characterization of Calcuim–activated Potassium Channels in Single Smooth Muscle Cells Using the Patch–clamp Technique", *Pflügers Archiv.*, 408, pp. 98–111 (1987).

Trivedi, S., et al., "Calcium Dependent K–Channels In Guinea Pig and Human Urinary Bladder", *Biochemical and Biophysical Research Communications*, 213, No. 2, pp. 404–409 (Aug., 1995).

Wilder Smith, A.E., "Preparation of Some New 4–Substituted Derivatives of p–Amino–o–hydroxy–phenyl–1,3, 4–oxadiazolone–5 and Study of their Mycobacteriostatic Activity", *Arzneim. Forsch.*, 67, No. 17, pp. 768–772 (1967).

*Primary Examiner*—Robert Gerstl
*Attorney, Agent, or Firm*—Aldo A. Algieri

[57] ABSTRACT

The present invention provides novel amino acid derivatives having the general formula

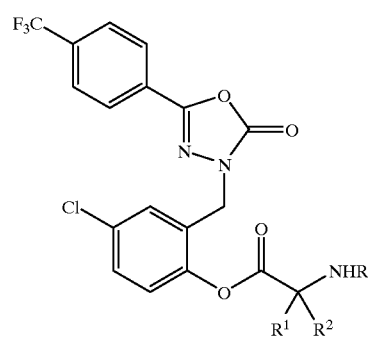

I wherein $R^1$, $R^2$ and $R^3$ are as defined herein, or a nontoxic pharmaceutically acceptable salt or solvate thereof and are useful in the treatment of disorders which are responsive to the opening of potassium channels.

13 Claims, No Drawings

AMINO ACID DERIVATIVES OF DIARYL 1,3,4-OXADIAZOLONE

CROSS-REFERENCE TO RELATED APPLICATION

This is a nonprovisional application which claims the benefit of provisional application U.S. Ser. No. 60/072,925, filed Jan. 29, 1998.

FIELD OF THE INVENTION

The present invention is directed to novel amino acid derivatives of a 1,3,4-oxadiazol-2(3H)-one compound which is a modulator of the large-conductance calcium-activated potassium (BK) channels and, therefore, useful in the protection of neuronal cells and diseases arising from dysfunction of cellular membrane polarization and conductance. The present invention also provides a method of treatment with the novel substituted oxadiazolone derivatives and to pharmaceutical compositions thereof.

BACKGROUND OF THE INVENTION

Stroke is presently recognized as the third leading cause of adult disability and death in the United States and Europe. In the past decade, several therapeutic approaches for the minimization of stroke-related brain damage have been pursued including inhibitors of AMPA/kainate, N-methyl-D-aspartate (NMDA) and adenosine reuptake inhibitors. It is the object of the present invention to provide novel compounds that will modulate potassium channels, in particular, large-conductance calcium-activated potassium (BK) channels which will be useful in reducing neuronal damage during ischemic conditions of a stroke episode.

Potassium channels play a key role in regulation of cell membrane potential and modulation of cell excitability. Potassium channels are themselves regulated by voltage, cell metabolism, calcium ion and receptor mediated processes. [Cook, N. S., *Trends in Pharmacol. Sciences*, 9, pp.21–28 (1988); and Quast, U. and Cook, N. S., *Trends in Pharmacol. Sciences*, 10, pp. 431–435 (1989)]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance <50 pS. ("pS" stands for picosiemen, a unit of electrical conductance.) Large-conductance calcium-activated potassium (BK) channels are present in many excitable cells including neurons, cardiac cells and various types of smooth muscle cells. [Singer, J. J. and Walsh, J. V., *Pflügers Archiv.*, 408, pp. 98–111 (1987); Baró,I., and Escande, D., *Pflügers Archiv.*, 414 (Suppl. 1), pp. S168–S170 (1989); and Ahmed, F. et al., *Br. J. Pharmacol.*, 83, pp. 227–233 (1984)].

Potassium ions play a dominant role in controlling the resting membrane potential in most excitable cells and in maintaining the transmembrane voltage near the $K^+$ equilibrium potential ($E_k$) of about −90 mV. It has been shown that opening of potassium channels shifts the cell membrane potential towards the equilibrium potassium membrane potential ($E_k$), resulting in hyperpolarization of the cell. [Cook, N. S., *Trends in Pharmacol. Sciences*, 9, pp. 21–28 (1988]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells under ischemic conditions.

The role of potassium channels in the operation of the smooth muscle of the human urinary bladder is discussed by S. Trivedi, et al. in *Biochemical and Biophysical Research Communications*, (1995), 213, No.2, pp. 404–409.

A range of synthetic and naturally occurring compounds with BK opening activity have been reported. The avena pyrone extracted from avena sativa-common oats has been identified as a BK channel opener using a lipid bi-layer technique [International Patent application WO 93/08800, published May 13,1993]. The flavanoid, Phloretin has been found to affect the opening of $Ca^{2+}$-activated potassium channels in myelinated nerve fibers of *Xenopus laevis* using outside-out patches [Koh, D-S., et al., *Neuroscience Lett.*, 165, pp.167–170 (1994)].

U.S. Pat. No. 3,971,803 issued to S. Rosenberger and K. Schwarzenbach on Jul. 27, 1976, relates to compounds of Formula (i):

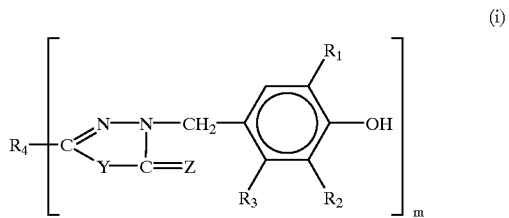

wherein $R_1$ is alkyl, cycloalkyl or aralkyl;

$R_2$ is hydrogen or $R_1$;

$R_3$ is hydrogen or $C_{1-4}$ alkyl;

Y and Z are independently O or S;

$R_4$ is either (1), if m=1, $C_{1-8}$ alkylene, —$C_xH_{2x}$—Q—$C_yH_{2y}$—(Q is O or S, x and y are integers whose sum is 2 to 4), phenylene, diphenylene or

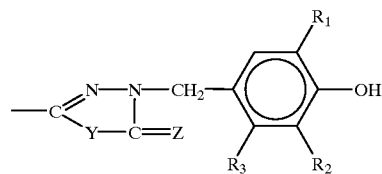

group;

or (2) if m=2, alkylene, alkylene ether, alkylene thioether, diphenylene, or napthalene. The compounds are antioxidants for organic polymers.

EPO 0-533276-A1 published on Mar. 24, 1993, shows compounds of Formula (ii):

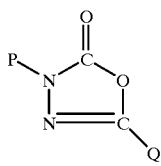

(ii)

wherein one of P or Q is an ortho-substituted phenyl group and the other a substituted benzyl. The Formula (ii) compounds are miticides and insecticides.

A. E. Wilder Smith disclosed in *Arzneim. Forsch.* (1967) 67, No.17, pp. 768–772, the preparation and study of compounds of Formula (iii):

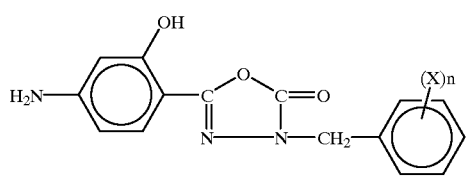

(iii)

wherein X is H or Cl and n is 1 or 2. The compounds have tuberculostatic properties. Formula (iii) compounds do not encompass substitution para to the hydroxyl group.

J. L. Romine, et al. in International Patent Application WO 98/04135, published Feb. 5, 1998, describe a series of diphenyl heterocycles of the Formula (iv):

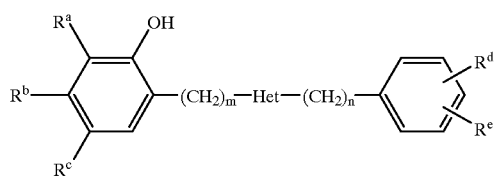

(iv)

wherein Het is a heterocyclic moiety selected from inter alia, oxadiazolone. The compounds are useful as modulators of the large conductance calcium-activated potassium channels and the starting material for the preparation of the compounds of the present invention is described therein wherein Het is 1,3,4-oxadiazol-2(3H)-one, m=1 and n=0, $R^c$ is chloro, $R^d$ is trifluoromethyl and $R^a=R^b=R^e$ is hydrogen.

None of these references teach or suggest the novel compounds of the present invention.

SUMMARY OF THE INVENTION

The present invention provides novel amino acid derivatives of 1,3,4-oxadiazolone having the general formula

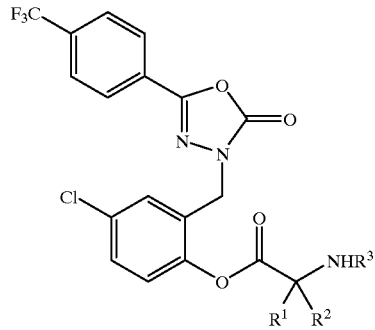

I wherein $R^1$, $R^2$ and $R^3$ are as defined below, or a nontoxic pharmaceutically acceptable salt or solvate thereof. The present invention also provides pharmaceutical compositions comprising said amino acid derivatives and to the method of treatment of disorders sensitive to potassium channel opening activity such as ischemia, stroke, convulsions, epilepsy, asthma, irritable bowel syndrome, migraine, traumatic brain injury, spinal cord injury, sexual dysfunction, and urinary incontinence.

DETAILED DESCRIPTION OF THE INVENTION

The present invention provides novel amino acid derivatives of 3-[(5-chloro-2-hydroxyphenyl)methyl]-5-[4-(trifluoromethyl)phenyl]-1,3,4-oxadiazol-2(3H)-one which is a potent opener of the large conductance, calcium-activated $K^+$-channels (Bk channel) and the novel derivatives have the general Formula I.

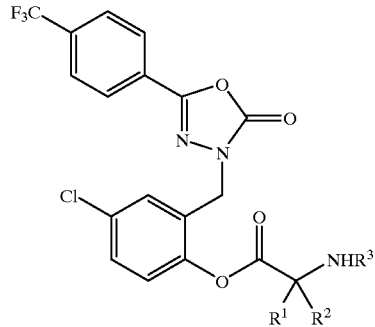

I wherein $R^1$ is hydrogen or methyl;

$R^2$ is hydrogen; or substituted or unsubstituted $C_{1-4}$ alkyl in which the substituent is selected from the group consisting of hydroxy, amino, methylthio, carboxyl, carboxamide, guanidino, phenyl or hydroxyphenyl; and $R^3$ is hydrogen or methyl; or $R^3$ and $R^2$ are joined together to form a pyrrolidinyl ring;

or a nontoxic pharmaceutically acceptable salt or solvate thereof.

The present invention also provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt thereof.

Preferably, the compounds of Formula I are useful in the treatment of ischemia, stroke, epilepsy, convulsions, asthma, irritable bowel syndrome, migraine, traumatic brain injury, spinal cord injury, sexual dysfunction, and urinary incontinence and other disorders sensitive to BK channel activating activity.

The term "$C_{1-4}$ alkyl" as used herein and in the claims (unless the context indicates otherwise) means straight or branched chain alkyl groups such as methyl, ethyl, propyl, isopropyl, butyl and isobutyl.

The term "a nontoxic pharmaceutically acceptable salt" as used herein and in the claims is intended to include nontoxic acid and base salts, and salts of zwitterionic species. Salts with a base is intended to include inorganic metallic salts such as sodium, potassium, calcium and magnesium, the ammonium salt, and salts with nontoxic amines such as trialkylamines, pyridine, picoline, dibenzylamine, ethanolamine, N-methylmorpholine and other amines which have been used to form salts of carboxylic acids. Suitable salts with an acid is intended to include inorganic acid salts such as hydrochloride, hydrobromide, hydroiodide, sulfate, phosphate, and the like, and organic acid salts such as formate, acetate, maleate, citrate, succinate, ascorbate, lactate, fumarate and tartrate which have been used to form salts of basic amines.

Unless otherwise specified, the term "amino acid" derivative as used herein means a naturally occurring amino acid. Suitable amino acids are those described herein and other known amino acids such as alanine, glycine, arginine, cysteine, isoleucine, leucine, lysine, valine, methionine, phenylalanine, threonine and the like. It should be appreciated by those skilled in the art that the compounds of Formula I wherein $R^1$ and $R^2$ contain an acyl residue of a naturally occurring amino acid may be active in vivo as a prodrug, i.e., the amino acid residue may be hydrolyzed by peptidase enzymes in the host to produce a more active form of the desired 1,3,4-oxadiazoline. Also, it should be appreciated by those skilled in the art that unnatural amino acids such as those in the D-configuration may be substituted for the natural occurring amino acids in the L-configuration.

Generally, pharmaceutically acceptable salts of the invention are those in which the counter anion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula I compound with the selected acid, preferably by contact in solution employing an excess of commonly used inert solvents such as water, ether, dioxane, methylene chloride, isopropanol, methanol, ethanol, ethyl acetate and acetonitrile. They may also be made by metathesis or treatment with an ion exchange resin under conditions in which the appropriate ion of a salt of the substance of the Formula I is replaced by another ion under conditions which allow for separation of the desired species such as by precipitation from solution or extraction into a solvent, or elution from or retention on an ion exchange resin.

Certain compounds of the present invention including the pharmaceutically acceptable salts thereof can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the composition that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

In another aspect, this invention provides water-soluble prodrugs of 3-[(5-chloro-2-hydroxyphenyl)methyl]-5-[4-(trifluoromethyl)phenyl]-1,3,4-oxadiazol-2(3H)-one which is described in WO 98/04135. As used herein the term prodrug denotes a derivative of an active drug which is converted after administration back to the active drug. More particularly, it refers to amino acid derivatives of 1,3,4-oxadiazol-2(3H)-one compounds which may be active drugs and/or which are capable of undergoing hydrolysis of the ester or cleavage of the ester so as to release active free drug. The physiologically hydrolyzable groups serve as prodrugs by being hydrolyzed in the body to yield the parent drug per se, and thus, the water-soluble prodrugs of the present invention are preferred for administration of the parent drug.

In still another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt, solvate or hydrate thereof. Preferably, the compounds of Formula I are useful in the treatment of ischemia, stroke, convulsions, epilepsy, asthma, irritable bowel syndrome, migraine, traumatic brain injury, spinal cord injury, urinary incontinence and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity. Most preferably, the compounds of Formula I are useful in the treatment of cerebral ischemia/stroke.

In still yet another aspect, this invention provides pharmaceutical compositions comprising at least one compound of Formula I in combination with a pharmaceutical adjuvant, carrier or diluent.

The compounds of Formula I may be prepared by various procedures such as those illustrated herein in the examples, in the Reaction Scheme and variations thereof which would be evident to those skilled in the art. The various prodrug compounds of Formula I may advantageously be prepared from the active drug substance of Formula II which is itself prepared by the general procedure described in WO 98/04135 and in Example I and used as the starting material in the methods illustrated in Reaction Scheme 1.

REACTION SCHEME 1

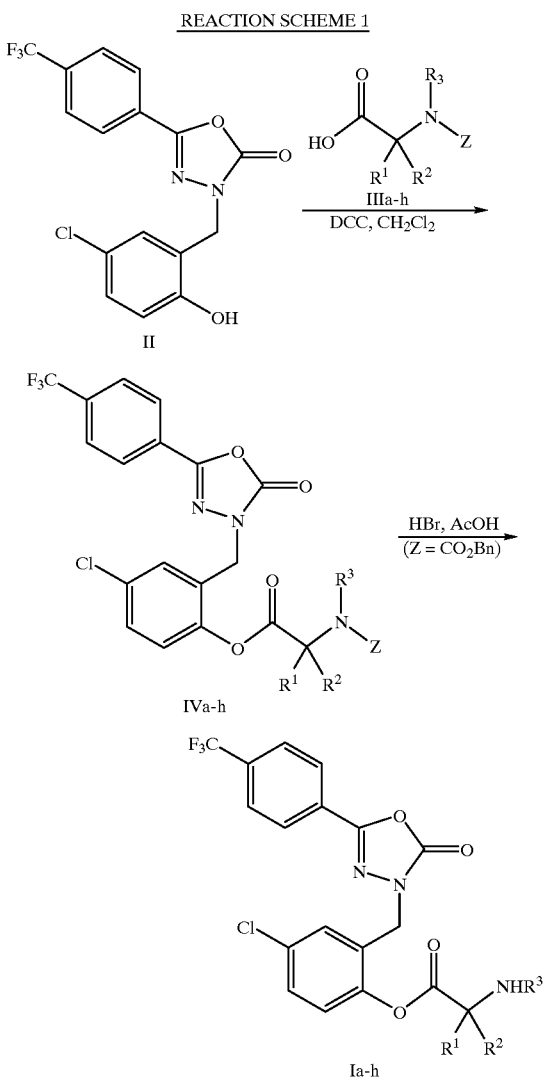

The preparation of amino acid esters of 1,3,4-oxadiazol-2-(3H)-one derivatives of Formula Ia–h, is illustrated in Reaction Scheme 1. When it is desired to prepare the amino acid ester compounds of Formula Ia–h, the compound of Formula II is treated with a N-carbobenzyloxy amino acid of Formula IIIa–h in an anhydrous inert organic solvent such as methylene chloride and the coupling is advantageously carried out in the presence of 1,3-dicyclohexylcarbodiimide (DCC) to produce the corresponding compound of Formula IVa–h. Deprotection of the carbobenzyloxy group (Z) of Formula IVa–h with HBr in acetic acid yields the HBr salt of the amino acid ester compound of Formula Ia–h.

In a preferred embodiment of the invention, the compounds have the Formula I

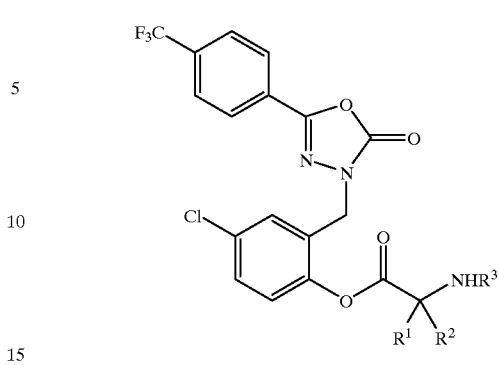

wherein $R^1$ and $R^3$ are hydrogen or methyl; $R^2$ is $C_{1-4}$ alkyl optionally substituted with hydroxy, amino, methylthio, carboxyl, carboxamide, guanidino, phenyl or hydroxyphenyl; and $R^2$ and $R^3$ may be joined together to form a pyrrolidinyl ring; or a nontoxic pharmaceutically acceptable salt or solvate thereof. Preferably, $R^1$ and $R^3$ are hydrogen and $R^2$ is $C_{1-4}$ alkyl or a nontoxic pharmaceutically acceptable salt or solvate thereof.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating ischemia, convulsions, epilepsy, asthma, irritable bowel syndrome, migraine, traumatic brain injury, spinal cord injury, male and female sexual dysfunction, urinary incontinence and especially stroke in a mammal in need thereof, which comprises administering to said mammal a therapeutically effective amount of a compound of Formula I or a nontoxic pharmaceutically acceptable salt, solvate or hydrate thereof.

Biological Activity

Potassium ($K^+$) channels are structurally and functionally diverse families of $K^+$-selective channel proteins which are ubiquitous in cells, indicating their central importance in regulating a number of key cell functions [Rudy, B., Neuroscience, 25, pp. 729–749 (1988)]. While widely distributed as a class, $K^+$ channels are differentially distributed as individual members of this class or as families. [Gehlert, D. R., et al., Neuroscience, 52, pp. 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the large-conductance $Ca^{2+}$-activated $K^+$ channels (BK or BK channels), is regulated by transmembrane voltage, intracellular $Ca^{2+}$, and a variety of other factors such as the phosphorylation state of the channel protein. [Latorre, R., et al., *Ann. Rev. Physiol.*, 51, pp. 385–399 (1989)]. The large, single channel-conductance (generally>150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., *J. Pharmacol. Exp. Ther.*, 267, pp.1277–1285 (1993)].

Openers of BK channels exert their cellular effects by increasing the open probability of these channels [McKay, M. C., et al., J. *Neurophysiol.*, 71, pp. 1873–1882 (1994); and Olesen, S. -P., *Exp. Opin. Invest. Drugs*, 3, pp.1181–1188 (1994)]. This increase in the opening of individual BK channels collectively results in the hyperpolarization of cell membranes, particularly in depolarized cells, produced by significant increases in whole-cell BK-mediated conductance.

The ability of the compound of Example 1 to open BK channels and increase whole-cell outward ($K^+$) BK-mediated currents was assessed under voltage-clamp conditions by determining their ability to increase cloned mammalian (mSlo or hSlo) BK-mediated outward current heterologously expressed in Xenopus oocytes [Butler, A., et al., *Science*, 261, pp. 221–224 (1993); and Dworetzky, S. I., et al., *Mol. Brain Res.*, 27, pp.189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., *J. Biol. Chem*, 265, pp. 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compound profiled did not effect non-BK native currents in the oocytes. The compound of Example 1 was shown in at least 5 oocytes at a concentration of 1 $\mu$M to increase BK current to 126% of control of IBTX-sensitive current. Recordings were accomplished using standard two-electrode voltage clamp techniques [Stuhmer, W., et al., *Methods in Enzymology*, 207, pp. 319–339 (1992)]; voltage-clamp protocols consisted of 500–750 ms duration step depolarizations from a holding potential of –60 mV to +140 mV in 20 mV steps. The experimental media (modified Barth's solution) consisted of (in mM): NaCl (88), $NaHCO_3$ (2.4), KCl (1.0), HEPES (10), $MgSO_4$ (0.82), $Ca(NO_3)_2$ (0.33), $CaCl_2$ (0.41); pH 7.5.

A rapid screen to determine the ability of prodrugs to hydrolyze and release the drug (compound of Example 1) is conducted as follows. A 1 mg/mL stock solution of the prodrug is prepared in distilled water or acetonitrile or PEG-400. Plasma from freshly collected rat or human blood is used in this assay. To 1 mL of plasma at 37° C. was added 10 $\mu$L of stock solution of prodrug and mixed gently. Immediately after the mixing, 100 $\mu$L of plasma was removed and quenched with 300 $\mu$L of acetontrile (Zero time sample). Samples were also obtained at 30 minutes and quenched immediately. The quenched samples were centrifuged to obtain a clear supernatant for analysis. The stock solution, T=0 and T=30 samples were analyzed by a HPLC assay that separates the drug from the prodrug. Based on the relative peak areas of prodrug and drug in these samples, different prodrugs are characterized as fast, moderate and slow release agents. For example, in this model, the compound of Example 9 was dissolved in PEG-400 at a concentration of 1 mg/mL and incubated at 10 $\mu$g/mL in fresh rat plasma at 37° C. Analysis of the solution 5 minutes after incubation indicated conversion of the compound of Example 9 to the compound of Example 1.

To determine the ability of the compounds of the present invention to reduce cell loss resulting from neuronal ischemia, a standard focal cerebral ischemia is induced by permanent occlusion of the left middle cerebral artery (MCA) and common carotid artery (CCA) with one hour occlusion of the right CCA in the Wistar rat. The surgeries are performed using the sub-temporal approach of A. Tamura, et al., *J. Cereb. Blood Flow Metab.*, 1, pp. 53–60, (1981) and its modifications [K. Osborne, et al., *J. Neurol Neurosurg. Psychiatry*, 50, pp. 402–410 (1987) and S. Menzies, et al., *Neurosurgery*, 31, pp. 100–107, (1992).]

The compound of Example 1 was evaluated in the focal stroke model involving permanent occlusion of the left MCA (MCAO) and CCA (CCAO) and temporary occlusion of the right CCA in the Wistar rat. This procedure results in a reliably large neocortical infarct volume that is measured by means of vital dye exclusion in serial slices through the brain 24 hours after MCAO. In the present test, compounds were administered using an i.v. or i.p. route of administration two hours after occlusion. For example, in this model the compound of Example 1 significantly reduced the cortical infarct volume by about 18% when administered intravenously (10 $\mu$g/kg) as a single bolus two hours after middle cerebral artery occlusion as compared to vehicle-treated (water) control.

The results of the above in vitro and in vivo tests demonstrate that the novel 1,3,4-oxadiazol-2(3H)-one compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, sexual dysfunction, and urinary incontinence and other disorders sensitive to BK channel activating activity. Most preferably, the compounds of Formula I are useful in the treatment of cerebral ischemia/stroke.

The compounds of Formula I or pharmaceutical compositions thereof are useful in the treatment, alleviation or elimination of disorders or other disorders associated with the BK channels. Such disorders include ischemia, stroke, convulsions, epilepsy, asthma, irritable bowel syndrome, migraine, traumatic brain injury, spinal cord injury, sexual dysfunction and urinary incontinence and other disorders sensitive to potassium channel openers.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences,* Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 ng/kg to 10 mg/kg body weight. For parenteral administration, the dose may be in the range of 0.1 ng/kg to 1.0 mg/kg body weight for intravenous administration. The active ingredient will preferably be administered either continuously or in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances, including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

DESCRIPTION OF SPECIFIC EMBODIMENTS

In the following examples, all temperatures are given in degrees Centigrade. Melting points were recorded on a Gallenkamp capillary melting point apparatus temperatures are uncorrected. Proton magnetic resonance ($^1$H NMR) was recorded on a Bruker AC 300. All spectra were determined in the solvents indicated and chemical shifts are reported in $\delta$ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M-H)– was determined on a Finnigen TSQ 7000. High resolution mass spectra was determined on a Kratos MS50 in FAB mode using cesium iodide/glycerol as internal reference. The element analysis are reported as percent by weight.

The following examples illustrate procedures for the preparation of starting materials, intermediates and methods for the preparation of products according to this invention. It should also be evident to those skilled in the art that appropriate substitution of both materials and methods disclosed herein will produce the examples illustrated below and those encompassed by the scope of this invention.

EXAMPLE 1

3-[(5-Chloro-2-hydroxyphenyl)methyl]-5-[4-(trifluoromethyl)phenyl]-1,3,4-oxadiazol-2(3H)-one Step A 5-[4-(Trifluoromethyl)phenyl]-1.3,4-oxadiazol-2 (3H)-one 4-(Trifluoromethyl)benzoic acid hydrazide (commercially available from Maybridge Chemicals) (5 g, 24.5 mmol) was taken up in THF (250 ml)/triethylamine (2.7 ml, 26 mmol) under N$_2$ and 1,1'-carbonyl-diimidazole (4.2 g, 26 mmol) added. The solution was stirred for 18 h at 24° C., concentrated, and the residue was taken up in ethyl acetate, washed with 1 N HCl solution, sat'd NaHCO$_3$ solution, and brine prior to drying (MgSO$_4$). Concentration gave 5 g (89%) of the title compound from which a sample was recrystallized from diethyl ether/hexanes: mp 214–216° C. MS m/z: 231 (MH$^+$).

IR (KBr) 3280, 1778, 1608, 1420, 1318, 1170, 1114 cm$^{-1}$;

$^1$H NMR (DMSO-d$_6$) $\delta$7.87 (2H, d, J=8.3 Hz), 7.96 (2H, d, J=8.3 Hz), 12.77 (1H, br.s);

Anal. Calcd. for C$_9$H$_5$F$_3$N$_2$O$_2$.064 H$_2$O: C, 46.74; H, 2.24; N, 12.11.

Found: C, 47.07; H, 2.10; N, 12.34.

Step B

3-[(5-Chloro-2-methoxyphenyl)methyl]-5-[4-(trifluoromethyl)-phenyl]-1,3,4-oxadiazol-2(3H)-one 5-[4-(Trifluoromethyl)phenyl]-1,3,4-oxadiazol-2(H)-one (11.75 g, 51 mmol) and 5-chloro-2-methoxybenzylbromide

[N. Meanwell, et al., *Bioorg. Med. Chem. Lett.* 6, pp. 1641–1646 (1996)] (12.0 g, 51 mmol) and 11.2 g (81 mmol) of potassium carbonate were added to $CH_3CN$ (300ml) under nitrogen and potassium iodide (0.2 g, 1.2 mmol) was added. The solution was refluxed for 16 h, cooled, poured into water (1500 ml) and stirred vigorously. The precipitate was filtered to give a solid which was recrystallized from $CH_3CN$ to give 15.2 g (78%) of the title compound.

mp 144–145° C. MS(ESI)m/z: 385 (MH$^+$).

IR (KBr) 3440, 1782, 1492, 1324, 1248, 1168 cm$^{-1}$;

$^1$H NMR (300 MHz, DMSO) δ3.79 (3H, s), 4.91 (2H, s), 7.07 (1H, d, J=8.8 Hz), 7.35–7.38 (2H, m), 7.88 (2H, d, J=8.4 Hz), 7.96 (2H, d, J=8.2 Hz);

Anal. Calcd. for $C_{17}H_{12}ClF_3N_2O_3 \cdot 0.1\ H_2O$: C, 52.81; H, 3.19; N, 7.25.

Found: C, 53.03; H, 3.20; N, 7.31.

Step C

3-[(5-Chloro-2-hydroxyphenyl)methyl]-5-[4-(trifluoromethyl)-phenyl]-1,3,4-oxadiazol-2(3H)-one 3-[(5-Chloro-2-methoxyphenyl)methyl]-5-[4-(trifluoromethyl)-phenyl]-1,3,4-oxadiazol-2(3H)-one (15.2 g, 39.6 mmol) was admixed with pyridine hydrochloride (19.7 g, 0.17 mol) and heated at 225° C. for 2 h. The hot solution was poured into 800 ml of 1 N HCl and the mixture was stirred for 10 min. The solid was collected, washed with 1 N HCl and dried at 80° C. under vacuum to afford 13.1 g of an off-white solid. Recrystallization from acetonitrile gave 10.8 g of the title compound as fluffy needles, mp 217–218° C. MS m/z: 371 (MH$^+$).

IR (KBr) 3354, 1762, 1500, 1324, 1068 cm$^{-1}$;

$^1$H NMR (DMSO-d$_6$) δ4.98 (2H, s), 6.84 (1H, d, J=8.7 Hz), 7.20 (1H, dd, J=8.7 Hz, 2.6 Hz), 7.30 (1H, d, J=2.5 Hz), 7.89 (2H, d, J=8.6 Hz), 7.97 (1H, d, J=8.6 Hz), 10.11 (1H, br.s);

Anal. Calcd. for $C_{16}H_{10}ClF_3N_2O_3$: C, 51.84; H, 2.72; N, 7.56.

Found: C, 51.88; H, 2.58; N, 7.57.

EXAMPLE 2

3-[(5-Chloro-2-hydroxyphenyl)methyl]-5-[4-(trifluoromethyl)phenyl]-1,3,4-oxadiazol-2(3H)-one, glycine ester (Ia, $R^1=R^2=R^3=H$)

Step A

3-[(5-Chloro-2-hydroxyphenyl)methyl]-5-[4-(trifluoromethyl)phenyl]-1,3,4-oxadiazol-2(3H-one, N-carbobenzyloxyglycine ester (IVa, $R^1=R^2=R^3=H$)

Neat 1,3-dicyclohexylcarbodiimide (DCC) (95 mg, 0.46 mmol) was added to stirred mixture of 3-[(5-chloro-2-hydroxyphenyl)methyl]-5-[4-(trifluoromethyl)phenyl]-1,3, 4-oxadiazol-2(3H)-one (170 mg, 0.48 mmol), N-carbobenzyloxyglycine (96 mg, 0.46 mmol) in anhydrous dichloromethane (5 mL) and maintained at room temperature overnight. Reaction mixture was diluted with dichloromethane (30 mL), and cool to 0° C. for 1 hr before it was filtered. The filtrate was evaporated and the residue was re-suspended in diethylether and then filtered. The filtrate was evaporated and the residue was recrystallized twice from diethylether/hexane to afford white needles (240 mg, 85%): mp 116–1180° C.; MS m/e 562 (MH$^+$).

$^1$H NMR (CDCl$_3$) δ4.35 (d, J=6 Hz, 2H), 4.84 (s, 2H), 5.14 (s, 2H), 5.52 (brd s, 1H), 7.10 (d, J=8.7 Hz, 1H), 7.30–7.40 (m, 6H), 7.51 (d, J=2.4 Hz, 1H), 7.68 (d, J=8.4 Hz, 2H), 7.89 (d, J=8.4 Hz, 2H).

Anal. calcd. for $C_{26}H_{19}ClF_3N_2O_6$: C, 55.58; H, 3.41; N, 7.48.

Found: C, 55.56; H, 3.46; N, 7.41.

Step B

3-[(5-Chloro-2-hydroxyphenyl)methyl]-5-[4-(trifluoromethyl)phenyl]-1,3,4-oxadiazol-2(3H)-one, glycine ester (Ia. $R^1=R^2=R^3=H$)

A mixture of 3-[(5-chloro-2-hydroxyphenyl)methyl]-5-[4-(trifluoromethyl)phenyl]-1,3,4-oxadiazol-2(3H)-one, N-carbobenzyloxyglycine ester (IVa) (237 mg, 0.42 mmol) and HBr (0.65 mL, 30% in acetic acid, 3.25 mmol) was stirred in acetic acid (3 mL) at room temperature for 2 hr. The resulting reaction mixture was evaporated and the residual solid was re-suspended in diethylether and then filtered, washed with diethylether and then dried in vacuo to afford a white solid (158 mg, 88%): mp 210–211° C. (dec.); MS m/e 428 (MH$^+$).

$^1$H NMR (DMSO-d$_6$) δ4.17 (s, 2H), 4.99 (s, 2H), 7.33 (d, J=8.7 Hz,1 H), 7.58 (dd, J=8.7, 2.4 Hz,1H), 7.71 (d, J=2.4 Hz,1H), 7.92 (d, J=8.4 Hz, 2H), 8.00 (d, J=8.4 Hz, 2H), 8.39 (brd m, 3H).

Anal. calcd. for $C_{18}H_{13}ClF_3N_2O_4 \cdot HBr$: C, 42.50; H, 2.77; N, 8.26.

Found: C, 41.67; H, 2.97; N, 8.02.

EXAMPLE 3

3-[(5-Chloro-2-hydroxyphenyl)methyl]-5-[4-(trifluoromethyl)phenyl]-1, 3,4-oxadiazol-2(3H)-one, (L)-Alanine ester (Ib)

The title compound was prepared using the general procedure described in Example 2. The crude product was triturated with hot ethyl acetate, cooled to room temperature and filtered. The resulting white needles were dried in vacuo (123 mg, 68% yield): mp 214–215° C.;

$^1$H NMR (DMSO-d$_6$) δ1.61 (d, J=7.2 Hz, 3H), 4.47 (m, 1H), 4.99 (s, 2H), 7.35 (d, J=8.7 Hz,1H), 7.58 (dd, J=8.7, 2.4 Hz,1H), 7.69 (d, J=2.4 Hz, 1H), 7.93 (d, J=8.4 Hz, 2H), 7.99 (d, J=8.4 Hz, 2H), 8.47 (brd m, 3H). MS m/e 442 (MH$^+$).

Anal. calcd. for $C_{19}H_{15}ClF_3N_2O_4 \cdot HBr$: C, 43.66; H, 3.09; N, 8.04.

Found: C, 43.39; H, 2.91; N, 7.80.

EXAMPLE 4

3-[(5-Chloro-2-hydroxyphenyl)methyl]-5-[4-(trifluoromethyl)phenyl]-1,3,4-oxadiazol-2(3H)-one, α,α-Dimethyl glycine ester (Ic)

The title compound was prepared by using the general procedure described in Example 2. The crude product was recrystallized from acetone/hexanes (146 mg, 82%): mp 167–168° C.; MS m/e 456 (MH$^+$).

$^1$H NMR (DMSO-d$_6$) δ1.70 (s, 6H), 5.00 (s, 2H), 7.37 (d, J48.7 Hz, 1H), 7.5 9 (dd, J=8.7, 2.4 Hz, 1H), 7.68 (d, J=2.4 Hz, 1H), 7.93 (d, J=8.7 Hz, 2H), 7.99 (d, J=8.7 Hz, 2H), 8.65 (brd m, 3H).

Anal. calcd. for $C_{20}H_{17}ClF_3N_2O_4 \cdot HBr$: C, 44.76; H, 3.38; N, 7.83.

Found: C, 45.11; H, 3.57; N, 7.46.

EXAMPLE 5

3-[(5-Chloro-2-hydroxyphenyl)methyl]-5-[4-(trifluoromethyl)phenyl]-1,3,4-oxadiazol-2(3H)-one, (L)-Leucine ester (Id)

The title compound was prepared by using the general procedure described in Example 2. The crude product was recrystallized from acetone/hexanes (156 mg, 78%): mp 195–1968° C.;

¹H NMR (DMSO-d₆) δ0.96 (d, J=4.5 Hz, 6H), 1.75–1.95 (m, 3H), 4.35 (m, 1H), 5.00 (dd, J=20, 12 Hz, 2H), 7.37 (d, J=8.7 Hz, 1H), 7.58 (dd, J=8.7, 2.4Hz, 1H), 7.69 (d, J=2.4 Hz, 1H), 7.93 (d, J=8.4 Hz, 2H), 7.99 (d, J=8.4 Hz, 2H), 8.54 (br, 3H). MS m/e 484 (MH⁺).

Anal. calcd. for $C_{22}H_{21}ClF_3N_2O_4 \cdot HBr$: C, 46.79; H, 3.93; N, 7.44.

Found: C, 47.08; H, 3.93; N, 7.16.

EXAMPLE 6

3-[(5-Chloro-2-hydroxyphenyl)methyl]-5-[4-(trifluoromethyl)phenyl]-1,3,4-oxadiazol-2(3H)-one, (L)-Lysine ester (1e)

The title compound was prepared by using the general procedure described in Example 2. The crude product was triturated with hot acetone with trace amount of ethyl acetate, cooled to room temperature, filtered and washed with acetone and diethylether. The resulting white powder was dried in vacuo (70%): mp 228–230° C.;

¹H NMR (DMSO-d₆) δ1.61 (brd m, 4H), 1.96–2.08 (m, 2H), 2.81 (brd m, 2H), 4.39 (brd s, 1H), 5.02 (s, 2H), 7.41 (d, J=8.7 Hz, 1H), 7.58 (dd, J=8.7, 2.4 Hz,1H), 7.69 (d, J=2.4 Hz,1H), 7.76 (brd m, 3H), 7.94 (d, J=8.7 Hz, 2H), 8.01 (d, J=8.7 Hz, 2H), 8.62 (brd m, 3H). MS m/e 499 (MH⁺).

Anal. calcd. for $C_{22}H_{22}ClF_3N_2O_4 \cdot 2HBr$: C, 39.99; H, 3.66; N, 8.48.

Found: C, 40.05; H, 3.60; N, 8.30.

EXAMPLE 7

3-[(5-Chloro-2-hydroxyphenyl)methyl]-5-[4-(trifluoromethyl)phenyl]-1,3,4-oxadiazol-2(3H)-one, (L)-Proline ester (1f)

The crude product was triturated with diethylether and trace amount of ethyl acetate and the resulting light yellow powder was dried in vacuo (180 mg, 38% for two steps). ¹H NMR (DMSO-d₆) δ1.98–2.04 (m, 2H), 2.30–2.50 (m, 2H), 3.30–3.37 (m, 2H), 4.76 (t, J=8.1 Hz, 1H), 5.02 (s, 2H), 7.45 (d, J=8.7 Hz, 1H), 7.59 (dd, J=8.7, 2.4 Hz, 1H), 7.70 (d, J=2.4 Hz, 1H), 7.93 (d, J=8.4 Hz, 2H), 7.99 (d, J=8.4 Hz, 2H), 8.24 (brd m, 2H). MS m/e 468 (MH⁺).

Anal. calcd. for $C_{21}H_{17}ClF_3N_2O_4 \cdot HBr$: C, 45.97; H, 3.31; N, 7.66.

Found: C, 45.36; H, 3.48; N, 7.44.

EXAMPLE 8

3-[(5-Chloro-2-hydroxyphenyl)methyl]-5-[4-(trifluoromethyl)phenyl]-1,3,4-oxadiazol-2(3H)-one, N-Methyl glycine ester (1g)

The title compound was prepared using the general procedure described in Example 2. The crude product was recrystallized from ethyl acetate (38% for two steps): mp 186–188° C.;

¹H NMR (DMSO-d₆) δ2.69 (s, 3H), 4.31 (s, 2H), 4.98 (s, 2H), 7.34 (d, J=8.7 Hz, 1H), 7.57 (dd, J=8.7, 2.7 Hz, 1H), 7.70 (d, J=2.7 Hz,1H), 7.91 (d, J=8.7 Hz, 2H), 7.99 (d, J=8.7 Hz, 2H), 9.08 (brd m, 2H). MS m/e 442 (MH⁺).

Anal. calcd. for $C_{19}H_{15}ClF_3N_2O_4 \cdot HBr$: C, 43.66; H, 3.09; N, 8.04.

Found: C, 44.27; H, 3.56; N, 7.58.

EXAMPLE 9

3-[(5-Chloro-2-hydroxyphenyl)methyl]-5-[4-(trifluoromethyl)phenyl]-1,3,4-oxadiazol-2(3H)-one, N-Methyl (L)-Leucine ester (1h)

The title compound was prepared by using the general procedure described in Example 2. The crude product was triturated in diethylether with trace amount of ethyl acetate and filtered. The resulting solid was recrystallized from acetone/hexanes (70% for two steps): mp 145–146° C.; MS m/e 498 (MH⁺).

¹H NMR (DMSO-d₆) δ0.97 (d, J=4.7 Hz, 6H), 1.80–2.01 (m, 3H), 2.73 (s, 3H), 4.40 (brd s,1H), 5.00 (dd, J=18, 16 Hz, 2H), 7.42 (d, J=8.7 Hz,1H), 7.58 (dd, J=8.7, 2.7 Hz,1H), 7.70 (d, J=2.7 Hz,1H), 7.93 (d, J=8.7 Hz, 2H), 7.99 (d, J=8.7 Hz, 2H), 9.27 (brd m, 2H).

Anal. calcd. for $C_{23}H_{23}ClF_3N_2O_4 \cdot HBr$: C, 47.73; H, 4.18; N, 7.26.

Found: C, 47.64; H, 4.41; N, 7.19.

What is claimed:

1. A compound of the formula

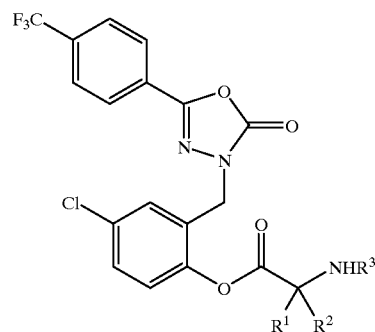

I wherein

R¹ is hydrogen or methyl;

R² is hydrogen; or substituted or unsubstituted $C_{1-4}$ alkyl in which the substituent is selected from the group consisting of hydroxy, amino, methylthio, carboxyl, carboxamide, guanidino, phenyl or hydroxyphenyl; and R³ is hydrogen or methyl; or R³ and R² are joined together to form a pyrrolidinyl ring;

or a nontoxic pharmaceutically acceptable salt or solvate thereof.

2. The compound of claim 1 wherein R¹, R² and R³ are hydrogen or a nontoxic pharmaceutically acceptable salt or solvate thereof.

3. The compound of claim 1 wherein R¹ and R³ are hydrogen and R² is methyl or a nontoxic pharmaceutically acceptable salt or solvate thereof.

4. The compound of claim 1 wherein R³ is hydrogen and R¹ and R² are methyl or a nontoxic pharmaceutically acceptable salt or solvate thereof.

5. The compound of claim 1 wherein R¹ and R³ are hydrogen and R² is 2-methylpropyl or a nontoxic pharmaceutically acceptable salt or solvate thereof.

6. The compound of claim 1 wherein R¹ and R³ are hydrogen and R² is aminobutyl or a nontoxic pharmaceutically acceptable salt or solvate thereof.

7. The compound of claim 1 wherein R¹ is hydrogen and R² and R³ are joined together to form a pyrrolidinyl ring or a nontoxic pharmaceutically acceptable salt or solvate thereof.

8. The compound of claim 1 wherein R¹ and R² are hydrogen and R³ is methyl or a nontoxic pharmaceutically acceptable salt or solvate thereof.

9. A compound of claim 1 wherein R¹ is hydrogen, R² is 2-methylpropyl and R³ is methyl or a nontoxic pharmaceutically acceptable salt or solvate thereof.

10. A pharmaceutical composition for the treatment of disorders responsive to openers of the large conductance calcium-activated potassium channels comprising a therapeutically effective amount of a compound as defined in claim 1 in association with a pharmaceutically acceptable carrier or diluent.

11. A method for the treatment of disorders responsive to opening of the large conductance calcium-activated potassium channels in a mammal in need thereof, which comprises administering to said mammal a therapeutically effective amount of a compound as defined in claim 1.

12. A method of claim 11 wherein said disorder is ischemia, stroke, convulsions, epilepsy, asthma, irritable bowel syndrome, migraine, traumatic brain injury, sexual dysfunction and urinary incontinence.

13. The method of claim 12 wherein the disorder is stroke.

* * * * *